April 21, 1953 R. ENGLE Plant Pat. 1,180
CARNATION PLANT
Filed Feb. 26, 1952
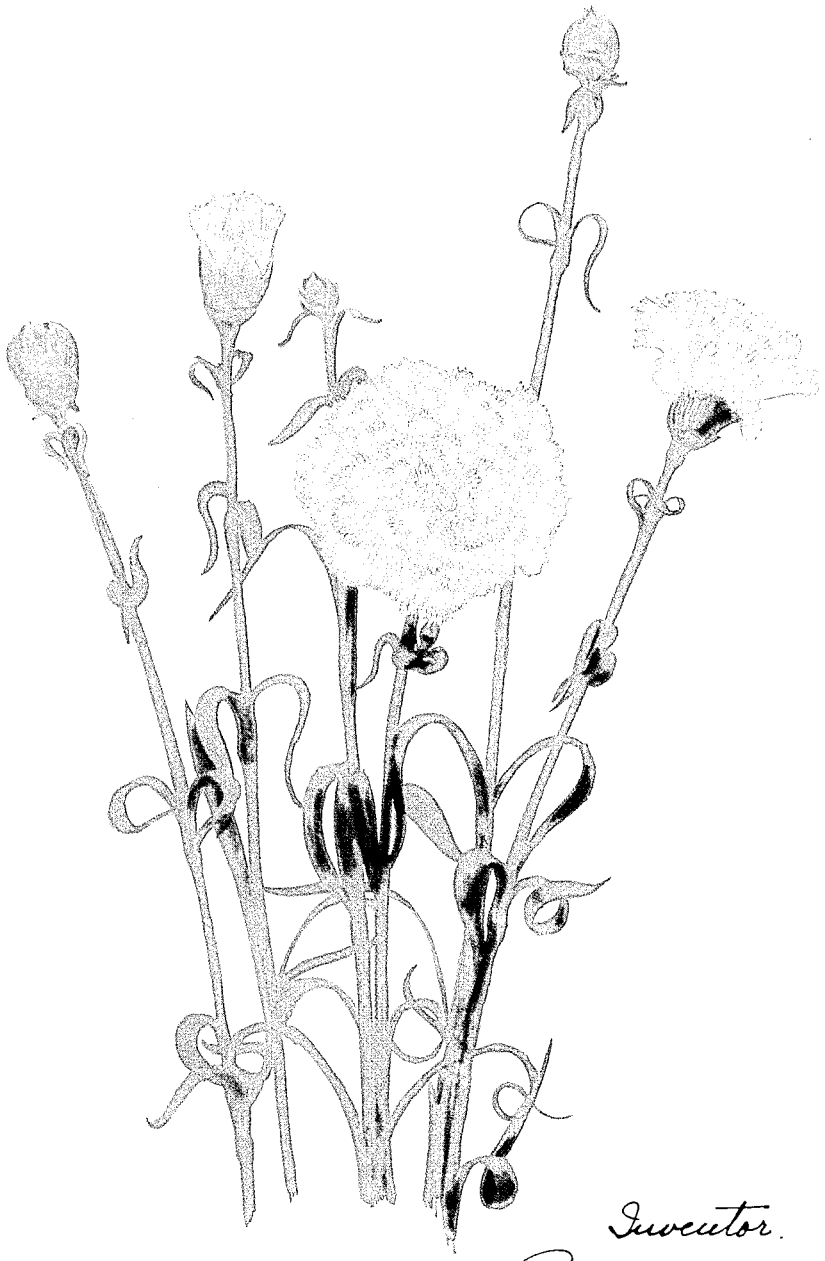
Inventor.
Russell Engle
By Robb & Robb
Attorneys Patented Apr. 21, 1953

Plant Pat. 1,180

UNITED STATES PATENT OFFICE 1,180

CARNATION PLANT

Russell Engle, Kokomo, Ind., assignor to Tom Knipe Florist, Kokomo, Ind., a partnership Application February 26, 1952, Serial No. 273,496

1 Claim. (Cl. 47—60)

The present invention relates to a new and distinct variety of carnation plant of the greenhouse type, originating as a sport of the variety known commercially as "Sarah Jane Knipe" (Plant Patent No. 909).

This new variety resulted from my continued efforts to improve carnations formerly grown in the greenhouses under my control at Kokomo, Indiana, and in which I have a partnership interest, where I have cross-pollinated many varieties, as well as subjected numerous varieties to special treatment involving the use of chemicals and various plant stimulants.

In the present instance, the new variety resulted specifically from the use of a chemical which I applied to a certain area of a plant of the variety "Sarah Jane Knipe," causing a mutation or growth branching from that area, and which was noticeably superior to the stems, foliage and flowers produced on the other areas of the plant. A cutting taken from the growth from the treated area was used to asexually reproduce the same and to produce additional plants of the new variety from which additional propagations have been made through several generations to date, at Kokomo, Indiana, by cuttings, all of which showed the same general characteristics of novelty, and thus fully establishing that these novel characteristics are firmly fixed and are transmissible through succeeding asexual propagations.

In comparison with the parent variety "Sarah Jane Knipe," my new variety bears heavier foliage, but its leaves are slightly longer; its stems are not quite as long as those of its parent, but are larger and stronger; and its flowers are from ½ inch to 1 inch larger in diameter. The flowers are nearly identical in color to those of the parent variety, but their substance is better. My new variety also propagates equally as well as the parent.

Microscopic tests of my new variety prove that it is a tetraploid, which apparently accounts for its vigorous habit of growth and for its large flowers.

The accompanying drawing shows specimens of my new carnation variety, with the stems, foliage and flowers in different stages of development.

The following is a detailed description of the new variety, with color terminology in accordance with Ridgway's Color Standards and Nomenclature:

*Plant*

Growth habits: Very strong root growth; branches freely from the base of the plant; average height three feet; roots easily and propagates well.

Blooming habits: Early and consistent in producing good quality blooms throughout the season.

Stem: Straight; unusually strong, with ample length; internodes average four inches in length and are the same color as the foliage.

Foliage: Ample; curled; averages five inches in length and three-eighths (⅜) inches wide. Color—near Terre Verte, Plate XXXIII.

*Flower*

Bud: Larger than average; one inch in length and three-fourths of an inch in diameter; petals appear light in color until they begin to unfold.

*Calyx.*—Single tube with five lobes; seldom splits.

*Color.*—Rinnemann's Green, Plate XVIII, fading to Mineral Green, Plate XVIII, at the very edges.

Bloom:

*Form.*—High-centered and compact.

*Color.*—Base color of petals Rhodamine Purple, Plate XII, fading to Mallow Purple, Plate XVII, and somewhat lighter at the very edges.

*Size.*—Large; measuring from 3¼ inches to 3¾ inches in diameter.

*Petalage.*—50 to 55 in number.

Petals:

*Texture.*—Unusually good; lacinated; crinkled at the end of the petals; average 1⅞ inches from calyx to tip and 1¼ inches at the widest point.

*Fragrance.*—Slightly cinnamon.

*Lasting qualities.*—Above the average.

*Bracts.*—Large; strong; same size as the calyx.

*Reproductive organs*

Ovaries: Medium in size; about ½ inch high and $\frac{5}{16}$ inch in diameter.

Pistils: Three or four in number; white and slightly curled at the tip; average 1 inch in length; seldom visible above the petals.

Stamens: Five to seven in number.

Filaments:

*Length.*—About 1 inch.

*Color.*—Mallow Purple, Plate XVII, at the tip, fading to White at the base.

Anthers:

*Size.*—Large.

*Color.*—Mallow Purple, Plate XVII.

I claim:

A new and distinct variety of carnation plant of the greenhouse type, substantially as herein shown and described, characterized as to novelty particularly by its heavy foliage and relatively long leaves, by its relatively large and strong stems, by its relatively large flowers, by the similarity in color of its flowers to those of its parent "Sarah Jane Knipe" (Plant Patent No. 909), by the improved substance of its flowers, and by its vigorous habit of growth and ease of propagation.

RUSSELL ENGLE.

No references cited.